United States Patent [19]

D'Urso

[11] Patent Number: 5,741,215

[45] Date of Patent: Apr. 21, 1998

[54] STEREOLITHOGRAPHIC ANATOMICAL MODELLING PROCESS

[75] Inventor: Paul Steven D'Urso, Coorparoo, Australia

[73] Assignee: The University of Queensland, St. Lucia, Australia

[21] Appl. No.: 596,237

[22] PCT Filed: Sep. 12, 1994

[86] PCT No.: PCT/AU94/00536

§ 371 Date: Apr. 25, 1996

§ 102(e) Date: Apr. 25, 1996

[87] PCT Pub. No.: WO95/07509

PCT Pub. Date: Mar. 16, 1995

[30] Foreign Application Priority Data

Sep. 10, 1993 [AU] Australia .................. PM1195

[51] Int. Cl.[6] .................. A61F 2/00; G06F 15/42
[52] U.S. Cl. .................. 600/407; 128/922; 128/898; 623/901; 378/901; 395/120
[58] Field of Search .................. 128/653.1, 920, 128/922, 898; 623/16, 66, 901; 378/4, 34, 901; 395/120, 121, 124, 125; 356/376, 379, 380

[56] References Cited

U.S. PATENT DOCUMENTS

| | | | |
|---|---|---|---|
| 4,436,684 | 3/1984 | White | 264/138 |
| 4,589,882 | 5/1986 | Urry | 623/11 |
| 4,902,290 | 2/1990 | Fleckenstein et al. | |
| 4,936,862 | 6/1990 | Walker et al. | |
| 4,953,087 | 8/1990 | Crawford | 364/413.18 |
| 4,976,737 | 12/1990 | Leake | 623/16 |
| 5,127,037 | 6/1992 | Bynum | |
| 5,217,653 | 6/1993 | Mashinsky | 264/22 |
| 5,231,470 | 7/1993 | Koch | 356/376 |
| 5,299,288 | 3/1994 | Glassman et al. | |
| 5,357,429 | 10/1994 | Levy | |
| 5,358,935 | 10/1994 | Smith et al. | |
| 5,373,860 | 12/1994 | Catone | |
| 5,443,510 | 8/1995 | Shetty et al. | |
| 5,452,407 | 9/1995 | Crook | |
| 5,454,383 | 10/1995 | Niblolon | |
| 5,487,012 | 1/1996 | Topholm et al. | |
| 5,554,190 | 9/1996 | Draenert | |
| 5,612,885 | 3/1997 | Love | |

FOREIGN PATENT DOCUMENTS

| | | |
|---|---|---|
| 0 574 099 | 12/1993 | European Pat. Off. |
| 89/10801 | 11/1989 | WIPO |
| 91/06378 | 5/1991 | WIPO |
| 92/08200 | 5/1992 | WIPO |

OTHER PUBLICATIONS

Pediatr. Radiol. (1992), 22: 458–460, "Pediatric craniofacial surgery: comparison of milling and stereolithography for 3D model manufacturing", H. M. Klein et al.

(List continued on next page.)

Primary Examiner—Marvin M. Lateef
Assistant Examiner—Shawna J. Shaw
Attorney, Agent, or Firm—Griffin, Butler, Whisenhunt & Szipl

[57] ABSTRACT

A method for stereolithographic construction of models including prostheses and anatomical pathology wherein CT scan data is computed to construct a plurality of two dimensional cross sectional images along one axis and the two dimensional image data is computed to create three dimensional coordinate data sets for the article to be modelled. The three dimensional data sets are then computed to obtain spaced parallel two dimensional image data sets in a second plane of the article and the reconstructed two dimensional image data sets are employed in a stereolithographic modelling apparatus to produce a three dimensional model of the article or part thereof. A prosthetic implant shaped to correct a defect in an anatomical part as well as a method for surgically implanting the implant using the stereolithographic method is also disclosed.

19 Claims, 4 Drawing Sheets

OTHER PUBLICATIONS

SPIE, vol. 1444, Image Capture, Formatting, and Display (1991), Solid models for CT/MR image display: accuracy and utility in surgical planning, Nicholas J. Mankovich et al (pp. 2–8).

Orthopaedic Clinics of North America, vol. 17, No. 4, Oct. 1986, Computer–Aided Simulation, Analysis, and Design in Orthopedic Surgery, Stephen B. Murphy, M.D. et al (pp. 637–649).

Australasian Physical & Engineering Sciences in Medicine, vol. 14, No. 1, 1991, "A Software System For Interactive and Quantitative Visualization of Multidimensional Biomedical Images", R. A. Robb et al (pp. 9–30).

STEREOLITHOGRAPHIC ANATOMICAL MODELLING PROCESS

FIELD OF INVENTION

THIS INVENTION is concerned primarily, but not exclusively, with methods and apparatus for forming implantable prostheses and method for use thereof.

BACKGROUND ART

A variety of methods and apparatus for three dimensional modelling of articles including prosthetic implants are known. Many of these techniques employ digitised information from CAD-CAM design systems or data captured and/or reconstructed from a variety of reflection and/or transmission scanning devices.

Such scanning devices include laser and acoustic reflection apparatus and various types of transmission apparatus including X-ray, magnetic resonance imaging (MRI), magnetic resonance angiography (MRA), positron emission (PET) as well as ultrasonic radiation. Typically, data is captured by scanning a series of spaced parallel planes which may then be combined by computer tomography (CT) techniques to reconstruct a two or three dimensional projection of the article so scanned.

Modelling of anatomical pathology using computed tomography data is well known for pre-operative planning and rehearsal of procedures and in the manufacture of prosthetic devices.

U.S. Pat. No. 4436684 describes a non invasive method for forming prostheses of skeletal structures for use in reconstructive surgery. Three dimensional coordinate data is obtained directly from the digital data generated by the computed tomographic information. The three dimensional coordinate data is then utilised to generate three dimensional cylindrical coordinates which are specified relative to an origin which is coincident with the origin of a coordinate system used in a sculpting tool apparatus to specify the spatial location of a cutting tool relative to a workpiece rotating on a turntable.

Due to difficulties in supporting the workpiece however it is generally not possible to sculpt an entire three dimensional model of an article, rather, this system is employed to construct models of portions of skeletal structures to act as male or female mould surfaces for construction of prosthetic inlays or onlays.

This apparatus and system however cannot construct a hollow model having faithfully reproduced external and internal surfaces and structural features.

U.S. Pat. No. 4976737 describes a method of forming a prosthetic device by employing the apparatus and method described in U.S. Pat. No. 4436684 to form a template which may be used directly or indirectly to create a mould surface for moulding a polyurethane impregnated Dacron (Trade Mark) prosthesis. This document describes in detail a "mirror imaging" technique to generate digital data for reconstruction of a missing, damaged or deformed portion of a skeletal structure by transferring image data from one side of an axis of symmetry to another.

Stereolithographic modelling of engineering components from UV sensitive cross-linkable acrylic polymers using CAD/CAM digital data is known. Of more recent times, the use of stereolithography for creation of three dimensional models of bony structures has been reported.

Stereolithographic modelling of anatomical pathology to provide a far more accurate means for physicians and surgeons to examine the condition of a patient for the purposes of diagnosis and for surgical procedures. Rather than rely upon say a solid model representing external features alone (as with U.S. Pat. No. 4436684), with or without two dimensional tomographic images, stereolithographically reproduced representations of anatomical pathology provide an almost exact replica of both internal and external features of a region under consideration.

Moreover, such stereolithographically reproduced models permit surgical procedures to be pre-planned and rehearsed with a great deal of precision to minimise risks and trauma and should enable a means for preparing accurate prostheses for surgical repair of defects or in reconstructive surgery.

One of the difficulties in reconstructing three dimensional co-ordinate data from X-ray tomographic scans is that in order to minimise the amount of radiation to which a patient is exposed, the tomographic "slices" are relatively widely spaced and complex computer programmes are required to reconstruct this scanning data. Typically a "slice" is about 1.5 mm in thickness and "slice" data is obtained at about 1.0 mm intervals. A scan of an adult human skull may thus comprise 70–80 tomographic "slices".

A comparison of three dimensional CT image reconstructions using a destructive mechanical milling process and a constructive stereolithographic modelling process is described in "Paediatric craniofacial surgery: Comparison of milling and stereolithography for 3D model manufacturing", *Pediatr. Radiol.* (1992) 22: 458–460. This article addresses the limitations of the milling process and concludes that while stereolithography is extremely expensive by comparison, "The slice oriented construction of the model corresponds well with the cross-sectional imaging methods and promises (sic) for the future a direct transfer from image slice to object slice."

Similar mechanical and stereolithographic modelling processes are described respectively in "Computed-Aided Simulation, Analysis, and Design in Orthopaedic Surgery", *Orthopaedic Clinics of North America*—Vol 17, No. 4, October 1986 and "Solid models for CT/MR image display: accuracy and utility in surgical planning", /SPIE Vol 1444 Image Capture, Formatting and Display (1991): 2–8.

Both of the references referred to immediately above describe in detail a computed tomography slice processing technique utilising proprietary software to trace all bone boundaries in the image volume after empirically determining the threshold for cortical bone. The algorithm, after exhaustively searching each image, locates the inner and outer edges of cortical bone objects and generates a contour volume data set. This data set is passed to a reformat program to generate the SLA build file containing information necessary to operate the stereolithography apparatus.

In both of these references, the technique requires that the exhaustive contour descriptions must be replicated four times to provide a finished layer of 0.25 mm in thickness. This repetition is necessary to reconstruct the CT axial resolution as one CT slice equals four SLA layers.

In transforming contour data to CAD data, a number of algorithms are available. A simple algorithm uses simple thresholded segmentation to produce voxel faces as paired triangles. A more complex technique uses the "Marching Cubes" algorithm which interpolates slices to yield a surface composed of sub-voxel polygons. The "Marching Cubes" algorithm is described in "Two algorithms for the three-dimensional reconstruction of tomograms", *Med Phys.* 15(3): 320–7, and "Marching Cubes: a high resolution 3D surface construction algorithm" *Computer Graphics.* 21:163–169.

In order to control the stereolithography apparatus for model construction contour information determined from tomograms this may be introduced into a CAD system to generate surface models composed of triangular approximations which is the standard interface between a CAD system and the stereolithography apparatus.

In addition to contour construction, the region between the inner and outer boundaries must be defined by hatch vectors to enable the solid region to be formed by cross linking of monomer in a predefined region in the monomer bath. By generating not only the contours, but also hatchings with different densities it is possible to produce different structures to represent cortical and trabecula bone.

Of more recent times however, there has been reported a more direct technique in "Medical Applications of Rapid Prototyping Techniques" :201–216.

This system addresses both the support generation and interpolation problems of earlier systems and is able to create directly from the CT scans the SLA files of both the model and its support structures in a much shorter time.

While it may be advantageous to utilise direct layer interfacing such that the most accurate directions of the input data in the scanning plane are produced on the most accurate directions of the stereolithography apparatus, the lack of true three dimensional data requires, as with the prior art systems, that the orientation of the part in the stereolithography apparatus should be the same as the orientation during the patient scanning operation.

There are a number of serious disadvantages associated with conventional manufacture of stereolithographic models in the same orientation as conventional patient scanning orientation.

As models are built up from successive 0.25 mm layers of polymerised resin, an upright model will take substantially longer to manufacture than a horizontally orientated model. For example, a 50 mm diameter cranial defect would require about 200 layers of polymerised material when in an upright position as against about 10–20 layers when the model is built in a horizontal orientation. Costs of model production could therefore be substantially reduced if manufacturing time could be reduced by selective orientation of models on the support platform in the monomer bath of the stereolithography apparatus.

Moreover, selective orientation of models during manufacture would permit a plurality of objects to be simultaneously modelled and orientated in the most efficient manner.

A further disadvantage is that with model construction limited to a single orientation, it is not possible to selectively orientate the model for construction to minimise the extent of support structure which must subsequently be removed from the completed model.

In all prosthetic implant surgery it is essential that a very close fit is obtained between the prosthesis and the tissue to which it is attached if an effective bond is to be obtained from tissue growth. Accordingly, there is a need for a much more accurate method for construction of prosthetic implants, both for hard and soft tissue regions, to ensure an initial accurate fit and accurate contour to avoid intraoperative delays while adjustments, contour changes or prolonged attachment procedures are undertaken.

It would also be advantageous in arterial and vascular surgery to provide complex branched prostheses which require attachment to blood vessels at the free ends of the prosthesis rather than having to construct the prostheses from tubular sections of varying diameters intraoperatively as is the case at present.

SUMMARY OF THE INVENTION

It is an aim of the present invention no provide an improved method for the construction of prosthetic implants and/or models of anatomical pathology.

It is another aim of the present invention to provide improved implantable prostheses.

It is yet a further aim of the invention to provide an improved method for implantation of prostheses.

According to one aspect of the invention there is provided a method for stereolithographic construction of implantable surgical prosthesis and/or an anatomical pathology model, said method comprising the steps of:

inputting into a data storage means scanning data relating to internal and/or external surfaces of anatomical pathology;

computing the stored scanning data according to a predetermined algorithm to reconstruct a plurality of two dimensional cross-sectional images of the anatomical pathology;

computing said plurality of two dimensional cross-sectional images according to a predetermined algorithm to generate a three dimensional coordinate data set for the anatomical pathology;

and generating a three dimensional representation of said anatomical pathology by stereolithographic modelling of a cross linkable liquid polymer using selected sequential two dimensional coordinate data sets computed in preselected planes from said three dimensional coordinate data set.

Suitably said scanning data comprises digitised X-ray, MRI, MRA, PET acoustic or other computed tomographic data.

If required the stored scanning data may be computed to reconstruct a plurality of two dimensional cross sectional images of an existing anatomical pathology.

Alternatively the stored scanning data may be computed to reconstruct a plurality of two dimensional cross-sectional images of an anatomical defect in a region of the pathology scanned.

If required, the two dimensional images of said defect may be generated by direct computation of image data obtained from a corresponding region on an opposite side of a symmetrical axis of a reconstructed two dimensional image.

Alternatively said two dimensional images of said defect may be generated by overlaying, in the defect region, an image obtained from an opposite side of a symmetrical axis of a reconstructed two dimensional image, assigning respective values to the image data obtained from opposite sides of said symmetrical axis and adding or subtracting the assigned values to obtain two dimension image data for the defect only.

If required, the two dimensional data obtained for the defect may be manipulated to obtain a best fit or enhanced fit with the defect region.

Preferably said method includes the step of simultaneously modelling a first portion of an anatomical pathology with an aperture defining the boundary of a defect and a second portion of said anatomical pathology complementary to said defect.

If required said second portion may be modelled with a peripheral boundary slightly larger than the peripheral boundary of said aperture.

The anatomical prosthesis may be constructed directly from a cross linkable polymer by stereolithographic modelling.

Preferably the liquid polymer is comprised of a biocompatible material, at least when cross linked.

Alternatively the prosthesis may be constructed indirectly by forming a mould from the stereolithographically formed anatomical pathology representation.

Preferably however the prosthesis may be constructed indirectly by manipulation of the scanned data, the reconstructed two dimensional images or the three dimensional coordinate data set to form a mould or mould surface from which the prosthesis may be moulded or otherwise formed.

According to another aspect of the invention there is provided a prosthetic implant whenever made in accordance with the aforesaid method.

The prosthetic implant may be comprised of an indirectly formed biocompatible metal such as titanium or the like.

The prosthetic implant may be constructed directly or indirectly from a biocompatible or bio-inert polymeric organic compound such as acrylic polymers and co-polymers, polyesters, polyolefins, polyurethanes, silicon polymers and co-polymers, vinyl polymers and co-polymers, halogenated hydrocarbons such as Teflon (Trade Mark), nylons etc. or even proteinaceous materials.

Preferably the prosthetic implant is constructed directly by stereolithographic modelling of a polymerisable or cross-linkable proteinaceous material.

If required the prosthetic implant may be constructed indirectly from an inorganic compound such as hydroxyapatite, ceramics or like materials.

Suitably the prosthetic implant is porous or comprises porous regions to permit bonding by tissue migration.

If required the prosthetic implant may be impregnated with tissue growth stimulation factors such as bone morphogenetic protein or the like.

The prosthetic implant may include mounting or attachment means to facilitate attachment to adjacent anatomical pathology.

According to yet another aspect of the invention, there is provided a method for the surgical implantation of a prosthesis comprising the steps of:

tomographically scanning a region of anatomical pathology;

inputting scanning data so obtained into a data storage means;

computing the stored scanning data according to a predetermined algorithm to reconstruct a plurality of two dimensional cross-sectional images of the anatomical pathology;

computing said plurality of two dimensional cross-sectional images according to a predetermined algorithm to generate a three dimensional coordinate data set for the anatomical pathology;

and generating a three dimensional representation of said anatomical pathology or a mould surface therefor by stereolithographic modelling of a cross linkable liquid polymer using selected sequential two dimensional coordinate data sets computed in preselected planes from said three dimensional coordinate data set; and surgically implanting in a patient a prosthesis obtained directly or indirectly therefrom, said prosthesis being characterised in having a close fit with connective tissue and contours appropriate for the implant site.

Preferably said three dimensional representation includes a region of anatomical pathology surrounding or adjacent to the region of anatomical pathology being modelled, said surrounding region providing a template for accurate fit of a prosthesis so obtained.

BRIEF DESCRIPTION OF THE INVENTION

In order that the various aspects of the invention may be more fully understood and put into practice, reference will now be made to various preferred embodiments illustrated in the drawings in which.

DETAILED DESCRIPTION

Figure 1:
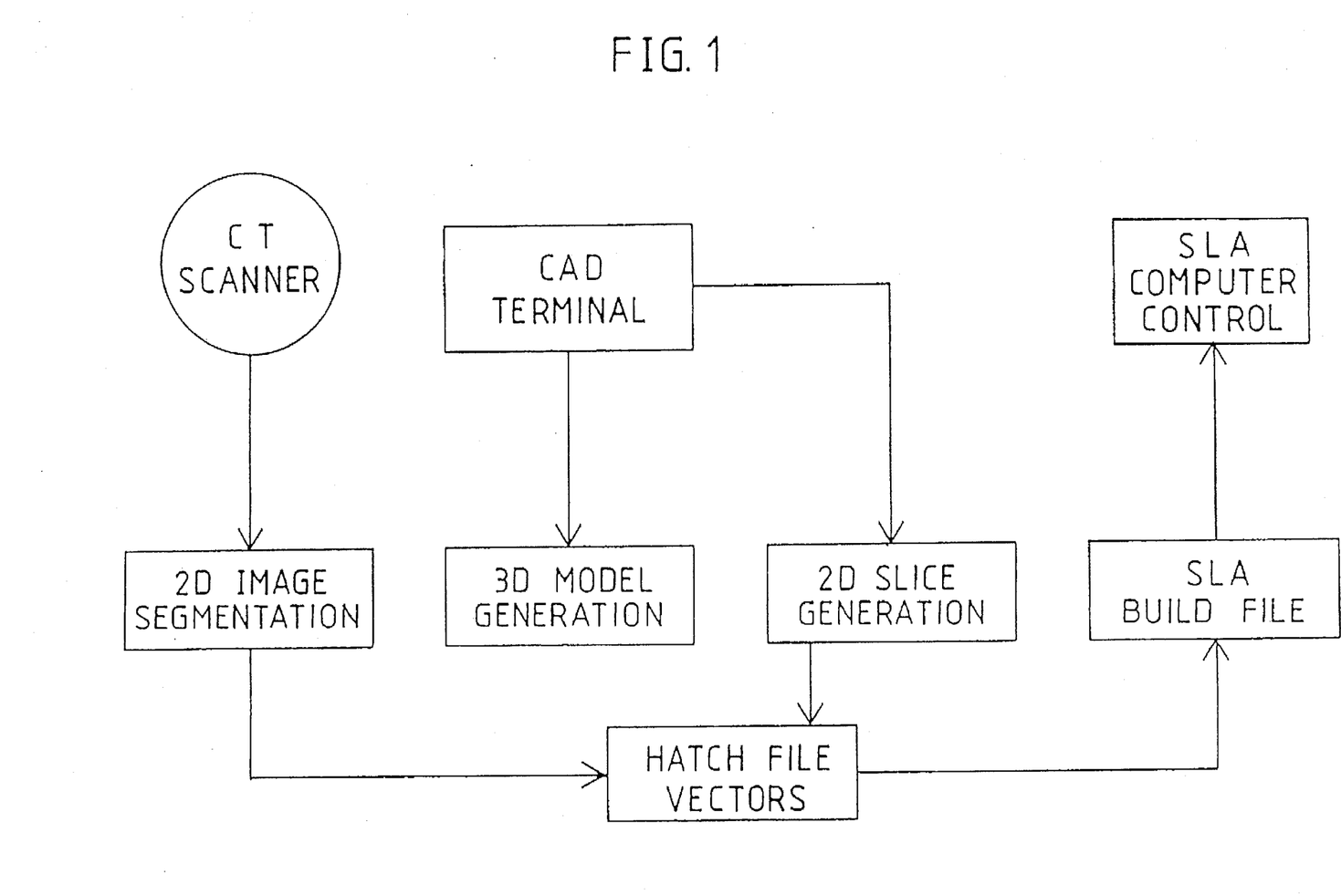
FIG. 1 shows schematically a data flow chart from capture through to operation of the SLA apparatus.

In FIG. 1 CT scan data is obtained conventionally from an X Ray, MRI, MRA, PET scanner and is processed by conventional software to produce, initially, two dimensional boundary images of say, a bony structure for each tomographic slice.

The segmented data is then further processed by conventional contour or voxel methods to produce a three dimensional data set for the anatomical pathology scanned. The three dimensional data set may be manipulated by conventional CAD software if so required.

The three dimensional data set is then further processed to produce parallel two dimensional slice image data sets, which can also be manipulated by the CAD software, before creation of the SLA build files required to operate the SLA apparatus.

Once the three dimensional data set is established, two dimensional slice data may be obtained at a selected spacing, suitably 0.25 mm to correspond to the model build layer thickness of the SLA apparatus.

For reasons which will be described in greater detail later, an operator is able to chose the planar orientation of the two dimensional slice data to optimise the SLA modelling operation rather than be constrained to generation of SLA build file data representing two dimensional data sets only in planes parallel to the tomography scan data as with prior art systems.

Hatch file vectors may be computed from the initial two dimensional segmented image data but preferably hatch file vectors are computed from the reconstructed two dimensional image data sets for the planar orientation chosen. This avoids the need for interpolation by repetition to create SLA build slices as with prior art systems. Moreover, the hatch file vectors are a more accurate representation of the solid structure for each individual SLA build slice.

Figure 2:
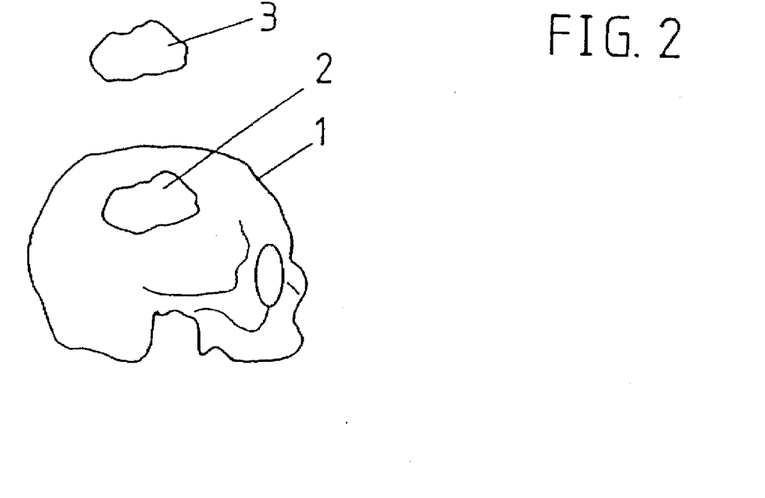
FIG. 2 shows a cranial defect and a prosthesis therefor.

FIG. 2 shows a human skull 1 with a cranial defect 2.

An ideal cranio-plastic implant 3 comprises a body of bio-compatible material which is shaped such that its thickness and contours are substantially identical to the bone which previously occupied the craniotomy defect. The peripheral shape is substantially identical to the peripheral shape of the defect aperture to permit a very close fit.

Accordingly, in a cranioplasty procedure, the previously manufactured cranio-plastic implant is able to be fitted directly to the defect and secured therein with acrylic cement, wires or screws. During such a procedure the operating time is minimised and the inherent risk of infection substantially reduced as little, if any, adjustments are necessary to adapt the implant to fit the defect.

Moreover the very close fit of the implant into the defect aperture minimises the degree of bone tissue growth required to bond with the implant to regain maximum structural integrity of the cranial structure.

The "ideal" cranio-plastic implant described with reference to FIG. 2 is obtained by a stereolithographic method in accordance with one aspect of the invention.

Initially, part or all of the cranial structure of a patient is scanned to obtain X-ray or MRI computed tomography data of spaced cross sections in a coronal or axial plane transverse to the long axis of the body due to the physical constraints of the scanning apparatus.

Using conventional computer software, the scanning data is segmented according to tissue type to define tissue boundaries and the segmented data is then reconstructed as two dimensional images in the same coronal plane.

Again, using conventional computer software the data relating to the reconstructed two dimensional images is computed and interpolated by voxel or contour means to generate three dimensional coordinate data sets which may be employed to display or print out two dimensional images of the three dimensional representation.

The three dimensional coordinate data sets may then be computed to generate two dimensional image data sets at much closer intervals than those representing the original coronal scan planes. Moreover, these two dimensional image data sets may be generated in any desired plane eg. sagittal, medial, coronal or other planes oblique to the main orthogonal planes.

Accordingly depending upon the position of the defect, two dimensional coordinate data sets may be established in one or more planes and the data sets may be combined to provide highly accurate three dimensional contour and shape definition in the region of the defect, particularly its boundaries.

Figure 3:
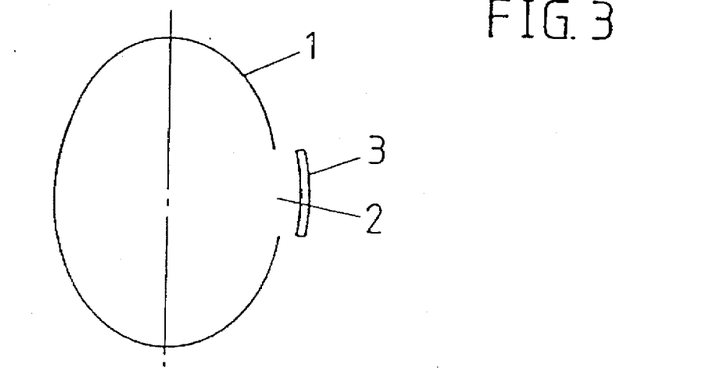
FIG. 3 shows a cross sectional view of a cranio-plastic implantation according to one method.

FIG. 3 shows one method for generating two dimensional coordinate data sets to construct three dimensional coordinate data sets for a cranio-plastic implant to be accommodated in the defect region 2.

From the closely spaced two dimensional images reconstructed from the computed three dimensional coordinate data sets, a two dimensional image may be drawn with a light pen or the like to fit the defect aperture. In so doing the drawn image follows a visual "best fit" mode in terms of thickness and contour. This procedure is repeated over a series of spaced parallel planes from the top of the defect to the bottom or vice versa.

The process may be repeated in a medial plane orthogonal to the first coronal plane to eliminate inaccuracies in say the upper and lower regions of the reconstructed image of the defect.

The combined image data representing three dimensional coordinate data for a cranio-plastic implant is assigned a numerical value as is the data representing the surrounding bone tissue. By appropriate allocation of respective values and then adding or subtracting those values, a three dimensional coordinate data set is obtained only for a structure representing a cranio-plastic implant.

The data so obtained is then employed with a stereolithographic apparatus to construct a model of an implantable prosthesis from a cross-linkable acrylic polymer.

Figure 4:
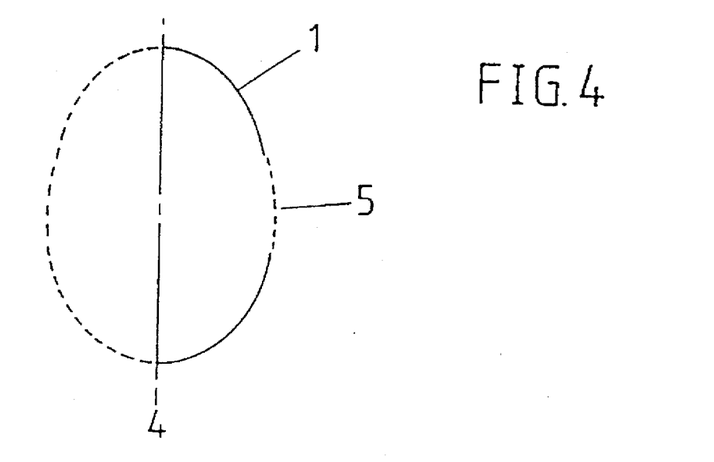
FIG. 4 shows a variation on the method of FIG. 2.

FIG. 4 shows an alternative method for construction of three dimensional coordinate data sets of a cranio-plastic implant.

In this method, two dimensional images are reconstructed from the three dimensional coordinate data sets at required planar spacings as with the method described above.

An axis of symmetry 4 is established relative to the two dimensional image and the bone tissue regions on each side of the axis are assigned arbitrary values of say +1 for the left side and −1 for the right side.

A mirror image of the left side is then superimposed on the right side image and the numerical values of the bone tissue regions are summed. The values for the intact portions of the cranial structure are nullified leaving an image 5 having a valve of +1 and representing a two dimensional cross sectional image of a plane in the region of the defect.

As most human cranial structures are not perfectly symmetrical there may be some misalignment of the mirror image object with the defect aperture. Using suitable graphics manipulation software or perhaps simply a light pen, corrections may be made as appropriate to align the superimposed image.

Figure 5:
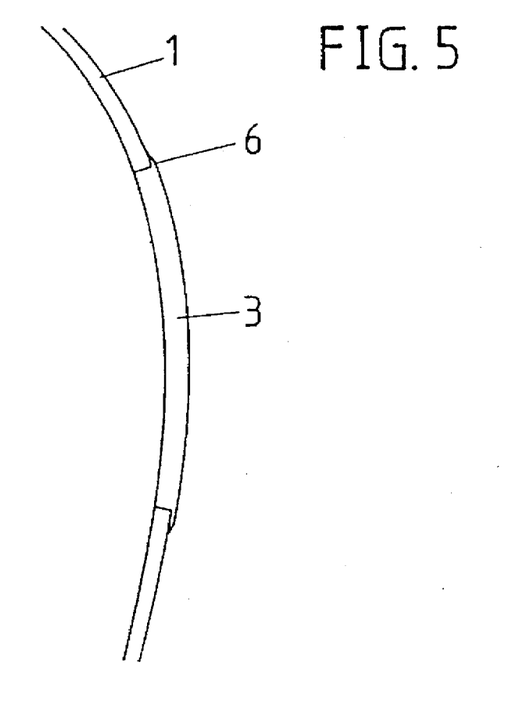
FIG. 5 shows a variation in the means of attachment of the cranio-plastic implant of FIGS. 2–4.

FIG. 5 shows yet another embodiment of the invention.

Using a graphics manipulation program, light pen or the like, the thickness of the three dimensional coordinate data for the implant may be increased, at least toward the peripheral edges. In this manner it is possible to build a smoothly tapered flange 6 around the periphery of the implant 3 to provide a more secure means of attachment to the surrounding bone tissue and otherwise permit a greater area for tissue bonding.

Suitably, the implant shown in FIG. 5 is constructed of a somewhat porous hydroxyapatite material and is impregnated in the region of flange 6 with bone morphogenetic protein to stimulate penetration of bone tissue into the implant.

Figure 6:
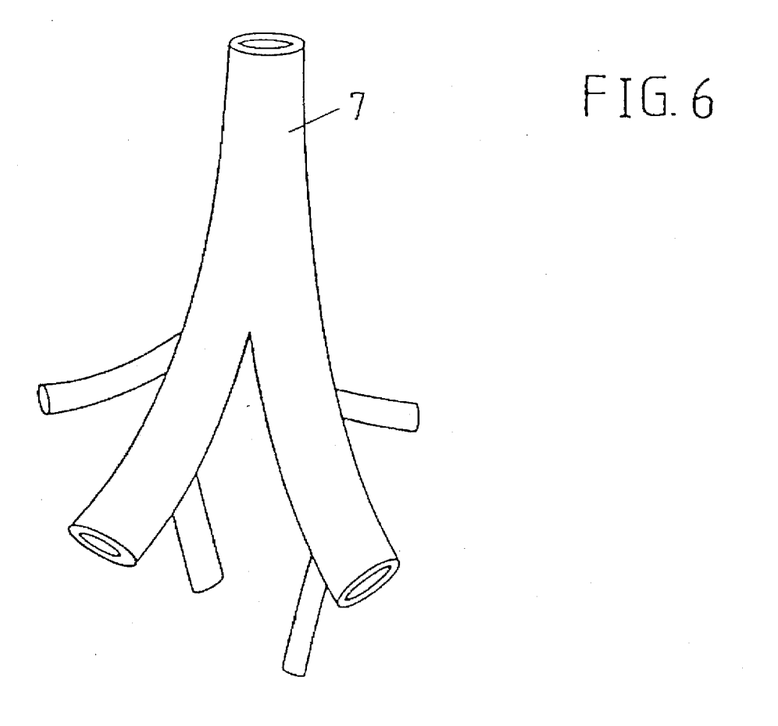
FIG. 6 shows a prosthetic replacement for an aortic junction aneurysm.

FIG. 6 illustrates a prosthetic implant 17 to replace an aortic junction, damaged for example by atherosclerosis and/or an aneurysm.

Using scanning data obtained from say MRI computed tomography, a complex hollow branched structure may be created directly using a flexible cross-linkable polymeric material in a stereolithographic apparatus. Where a region of wall thickness in the patient's aortic junction is reduced or damaged by the aneurism, this can be corrected or compensated for by manipulating the initial or reconstructed two dimensional scan images in a manner similar to that described with reference to FIGS. 3 and 4.

Alternatively the implant may be created indirectly by creating a female mould by a stereolithographic process, the mould having an internal surface corresponding to the external dimensions and contours of a computed three dimensional representation. The implant may be formed in the mould by, say, rotational casting of a thermoplastic material or a cross-linkable liquid polymer.

Arterial and vascular implants constructed in accordance with the invention have the advantage that operation time is substantially reduced, the number of sutured joins, sutures and suturing time is also substantially reduced and the free ends of the implant are substantially identical in diameter to the artery or vein to which they are to be attached.

Figure 7:
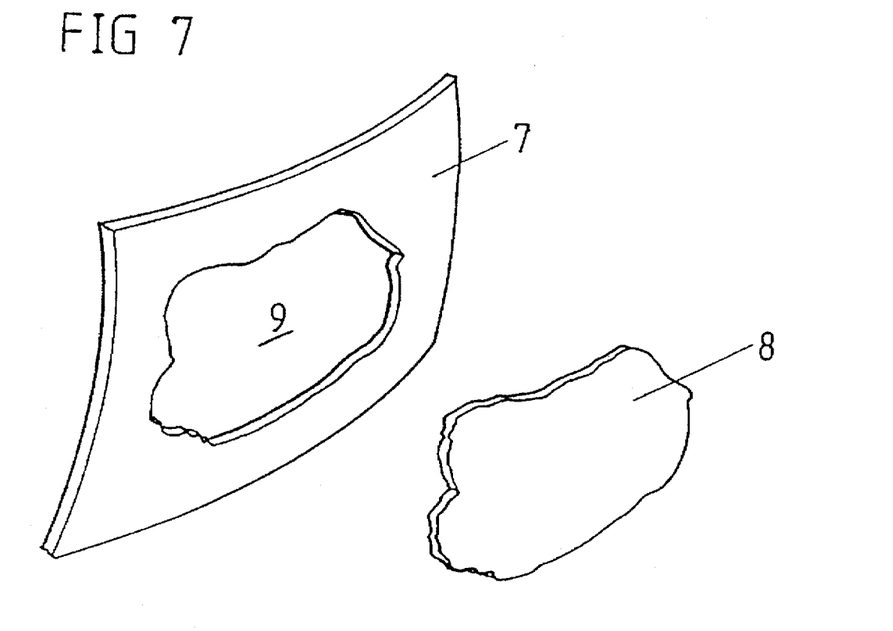
FIG. 7 shows an alternative method of production of a cranioplastic model.

FIG. 7 illustrates a most preferred method of creating a defect prosthesis such as a cranioplastic implant.

After establishing a three dimensional coordinate data set for a region 7 surrounding the defect 2, two dimensional image date is then reconstructed in spaced parallel planes generally perpendicular to the notional "surface" of region 7. By orienting the reconstructed two dimensional images in this manner highly accurate boundary definitions are obtainable for the edge of the effect aperture as well as the cross sectional contours of region 7.

A prosthetic model for the defect is then created by a computer program and when complete, the hatch file vectors are computed for each two dimensional image spaced at intervals corresponding to each SLA build slice.

An even more accurate two dimensional image data set may be obtained by selecting two reconstructed two dimensional image sets in planes orthogonal to each other and the "notional" surface of the defect. These orthogonal data sets may be combined to provide corrected two dimensional image sets in a selected plane.

With the reconstructed two dimensional image sets and the hatch file vectors obtained therefor, the SLA apparatus simultaneously builds models of the defect surround region 7 and the defect adjacent each other on the monomer bath table. When completed, the defect model 8 should be a very neat fit into the aperture 9 in surround region 7. If required, the defect model 8 may be trimmed with a file or built up with a hardenable putty to improve the fit in aperture 9.

In generating the reconstructed two dimensional image data, the peripheral edge of defect model 8 may be increased to provide a body of material for subsequent trimming.

Once a satisfactory fit of model 8 in aperture 9 has been achieved, a cranioplastic implant may then be manufactured from model 8 in acrylic or hydroxyapatite or other suitable material.

During a subsequent cranioplasty procedure, open wound time is minimised by avoiding the need for intraoperative manipulation or adjustment of the implant. Furthermore, the highly accurate fit of the implant permits a far more secure location of the implant with only minimal marginal gaps for bone regrowth.

Figure 8:
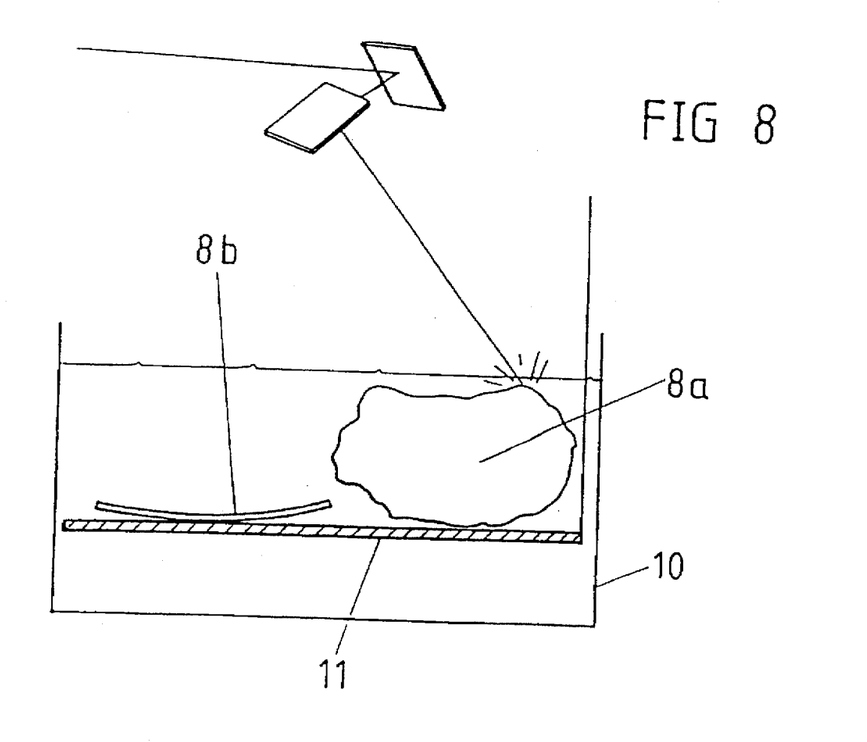
FIG. 8 shows alternative methods of orientation of a model in an SLA monomer bath.

FIG. 8 illustrates a particular advantage of the invention.

As prior art SLA processes are limited to modelling in slices parallel to the initial tomographic scan planes, this can lead to inefficiencies.

For example, as most bony structures such as arms, legs, hands etc. are scanned in a plane perpendicular to the longitudinal axis of the bones, SLA models of these bones are built in the direction of the longitudinal axis.

In the SLA modelling process, layers of polymerised monomer are built with a thickness of about 0.25 mm. Between each layer polymerising step, the support platform in the monomer bath is lowered and positioned at a predetermined distance below the level of monomer and certain delays are encountered in these steps whilst awaiting stabilisation of the monomer surface. In the modelling of a human skull built on coronal planes for example, the modelling process may take up to 36 hours.

According to the present invention, reconstructed two dimensional data sets for operation of the SLA apparatus may be selected in any suitable plane. Thus, in the monomer bath 10, the cranioplastic implant model 8 shown in FIG. 7 may be constructed in an upright manner represented by model 8a or in a generally horizontal position represented by model 8b. It can be seen therefore that the time normally required to produce model 8a can now be reduced by an amount proportional to the ratio between minimum and maximum supported dimensions.

Another advantageous feature of the present invention which arises from the choice of orientation of SLA slices of three dimensional data sets is that a plurality of models may be created simultaneously on the surface of the support platform 11 of the SLA apparatus. By careful selection of the plane of orientation of the reconstructed two dimensional data sets, the area of coverage of platform 11 and the model height may be chosen to optimise model construction time and/or to minimise the formation of support structures for "floating" artefacts during model build steps.

Moreover, selective orientation of model build directions permits support structures to be confined, say, to a posterior surface of an anatomical pathology when an accurately represented model of an anterior surface is required or vice versa.

With the development of cross-linkable or polymerisable biocompatible materials, it is envisaged many prosthetic implants may be constructed directly by the stereolithographic modelling process rather than in a two or three step method requiring the use of male or female moulds.

Moreover, complex reconstructive surgical procedures may be greatly simplified by the ability to pre-form complete prosthetic implants without the need to obtain donor tissue from other parts of the patients body. Under these circumstances a prolonged series of reconstructive procedures may perhaps be replaced with a single procedure.

It will be readily apparent to a skilled addressee that many modifications and variations may be made to the various aspects of the invention without departing from the spirit and scope thereof and that the methods according to the invention may be adapted for use in constructing a wide variety of models of anatomical pathologies as well as other structure.

For example, although an elongate article such as, say, a turbine blade may be required to be initially scanned at spaced intervals along the longitudinal axis, the transverse two dimensional scan data so obtained may be reconstructed initially as a three dimensional coordinate data set from which new longitudinal two dimensional data sets are computed. These new longitudinal two dimensional data sets are computed in parallel planes with a spacing of say 0.25 mm corresponding with the build layer thickness of the SLA apparatus.

Clearly, by building an SLA model such as a turbine blade along its longitudinal axis in a horizontal position, substantial cost savings can be obtained compared to prior art builds on an upright longitudinal axes.

I claim:

1. A method for stereolithographic construction of models including an implantable surgical prosthesis and/or an anatomical pathology model, said method comprising the steps of:

inputting into a data storage means scanning data relating to internal and/or external surfaces of anatomical pathology;

computing the stored scanning data according to a predetermined algorithm to reconstruct a plurality of parallel two dimensional cross-sectional images of the anatomical pathology;

computing said plurality of two dimensional cross-sectional images according to a predetermined algorithm to generate a three dimensional co-ordinate data set for the anatomical pathology; and generating a three dimensional representation of said anatomical pathology by stereolithographic modelling of a cross linkable liquid polymer using selected sequential two dimensional image data sets computed from said three dimensional co-ordinate data set, said two dimensional image data sets being computed in parallel planes which are not parallel to the planes in which said two dimensional cross-sectional images are obtained by scanning.

2. A method as claimed in claim 1 wherein said two dimensional image data sets are computed in parallel planes at closer intervals than planes in which said two dimensional cross-sectional images are obtained by scanning.

3. A method as claimed in claim 1 wherein said scanning data comprises digitised X-ray, MRI, MRA, PET, acoustic or other computed tomographic data.

4. A method as claimed in claim 1 wherein the stored scanning data is computed to reconstruct a plurality of two dimensional cross-sectional images of an anatomical defect in a region of the pathology scanned.

5. A method as claimed in claim 4 wherein the two dimensional images of said defect are generated by direct computation of image data obtained from a corresponding region on an opposite side of a central axis of a reconstructed two dimensional image.

6. A method as claimed in claim 4 wherein said two dimensional images of said defect are generated by overlaying, in the defect region, an image obtained from an opposite side of a central axis of a reconstructed two dimensional image, assigning respective values to the image data obtained from opposite sides of said central axis and adding or subtracting the assigned values to obtain two dimensional image data for the defect only.

7. A method as claimed in claim 4 including the step of simultaneously modelling a first portion of an anatomical pathology with an aperture defining the boundary of a defect and a second portion of said anatomical pathology complementary to said defect.

8. A method as claimed in claim 7 wherein said second portion is modelled with a peripheral boundary slightly larger than the peripheral boundary of said aperture.

9. A method as claimed in claim 1 wherein an anatomical prosthesis is constructed directly from a cross linkable polymer by stereolithographic modelling.

10. A method according to claim 1 wherein the prosthesis is constructed indirectly by forming a mould from a stereolithographically formed anatomical pathology representation.

11. A method according to claim 1 wherein the prosthesis is constructed indirectly by manipulation of the scanned data, the reconstructed two dimensional images or the three dimensional co-ordinate data set to form a mould or mould surface from which the prosthesis is moulded or otherwise formed.

12. A method for the surgical implantation of a prosthesis comprising the steps of:

tomographically scanning a region of anatomical pathology;

inputting scanning data so obtained into a data storage means;

computing the stored scanning data according to a predetermined algorithm to reconstruct a plurality of parallel two dimensional cross-sectional images of the anatomical pathology;

computing said plurality of two dimensional cross-sectional images according to a predetermined algorithm to generate a three dimensional co-ordinate data set for the anatomical pathology;

generating a three dimensional representation of said anatomical pathology or a mould surface therefor by stereolithographic modelling of a cross linkable liquid polymer using selected sequential two dimensional image data sets computed from said three dimensional co-ordinate data set, said two dimensional image data sets being computed in parallel planes which are not parallel to the planes in which said two dimensional cross-sectional images are obtained by scanning; and surgically implanting in a patient a prosthesis obtained directly or indirectly therefrom, said prosthesis being characterized in having a close fit with connective tissue and contours appropriate for an implant site.

13. A method as claimed in claim 12 wherein said three dimensional representation includes a region of anatomical pathology surrounding or adjacent to the region of anatomical pathology being modelled, said surrounding region providing a template for accurate fit of a prosthesis so obtained.

14. A method as claimed in claim 12 including the step of simultaneously modelling a first portion of an anatomical pathology with an aperture defining the boundary of a defect and a second portion of said anatomical pathology complementary to said defect.

15. A method as claimed in claim 14 wherein said second portion is modelled with a peripheral boundary slightly larger than the peripheral boundary of said aperture.

16. A method as claimed in claim 12 wherein an anatomical prosthesis is constructed directly from a cross linkable polymer by stereolithographic modelling.

17. A method according to claim 12 wherein the prosthesis is constructed indirectly by forming a mould from a stereolithographically formed anatomical pathology representation.

18. A method according to claim 12 wherein the prosthesis is constructed indirectly by manipulation of the scanned data, the reconstructed two dimensional images or the three dimensional co-ordinate data set to form a mould or mould surface from which the prosthesis is moulded or otherwise formed.

19. A method as claimed in claim 12 wherein said two dimensional image data sets are computed in parallel planes at closer intervals than planes in which said two dimensional cross-sectional images are obtained by scanning.

* * * * *